(12) United States Patent
Osborne (10) Patent No.: US 11,479,815 B2
(45) Date of Patent: Oct. 25, 2022

(54) METHOD FOR BIDIRECTIONAL SEQUENCING

(71) Applicant: OXFORD NANOPORE TECHNOLOGIES PLC, Oxford (GB)

(72) Inventor: Robert Osborne, Saffron Walden (GB)

(73) Assignee: OXFORD NANOPORE TECHNOLOGIES PLC, Oxford (GB)

( * ) Notice: Subject to any disclaimer, the term of this patent is extended or adjusted under 35 U.S.C. 154(b) by 331 days.

(21) Appl. No.: 15/756,050

(22) PCT Filed: Sep. 1, 2016

(86) PCT No.: PCT/IB2016/055251
§ 371 (c)(1),
(2) Date: Feb. 27, 2018

(87) PCT Pub. No.: WO2017/037656
PCT Pub. Date: Mar. 9, 2017

(65) Prior Publication Data
US 2018/0245148 A1 Aug. 30, 2018

(30) Foreign Application Priority Data
Sep. 2, 2015 (GB) .................................... 1515557

(51) Int. Cl.
*C12P 19/34* (2006.01)
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

2003/0157489 A1* 8/2003 Wall ...................... G16B 30/20
435/6.12
2010/0310520 A1* 12/2010 Sanz Herranz ...... A61K 35/745
424/93.4
(Continued)

FOREIGN PATENT DOCUMENTS

WO    WO 2015/083004    6/2015

OTHER PUBLICATIONS

"Introduction to Phased Sequencing". Printed on Dec. 10, 2021.*
(Continued)

*Primary Examiner* — Frank W Lu
(74) *Attorney, Agent, or Firm* — James S. Keddie; Bozicevic, Field & Francis LLP (57) ABSTRACT

Described herein is a method of sequencing, comprising: splitting an asymmetrically tagged library into a plurality of subsamples, tagging the adaptor-ligated DNA in the subsamples with sequence tags that identify the subsamples, optionally pooling the sub-samples, sequencing polynucleotides from each of the tagged sub-samples, or copies of the same, to produce sequence reads each comprising: i. a sub-sample identifier sequence and ii. the sequence of at least part of a fragment in the sample, wherein some of the sequence reads are derived from the top strand of a fragment in the sample and some of the sequence reads of are derived from the bottom strand of the same fragment.

14 Claims, 4 Drawing Sheets

(56) References Cited

U.S. PATENT DOCUMENTS

| | | | |
|---|---|---|---|
| 2013/0157870 A1 | 6/2013 | Pushkarev et al. | |
| 2014/0287937 A1* | 9/2014 | So | C12Q 1/6886 |
| | | | 506/7 |
| 2015/0024950 A1* | 1/2015 | Bielas | C12N 15/70 |
| | | | 506/4 |
| 2015/0044687 A1 | 2/2015 | Schmitt et al. | |
| 2018/0002747 A1* | 1/2018 | Druley | C12Q 1/6858 |

OTHER PUBLICATIONS

Kennedy et al., "Detecting ultralow-frequency mutations by Duplex Sequencing", Nat. Protoc., 2014, 9(11): 2586-2606.

Kinde et al., "Detection and quantification of rare mutations with massively parallel sequencing", Proceedings of the National Academy of Sciences, 2011, 108(23): 9530-9535.

Meacham et al., "Identification and correction of systematic error in high-throughput sequence data", BMC Bioinformatics, 2011, 12:451.

Neiman et al., "Library Preparation and Multiplex Capture for Massive Parallel Sequencing Applications Made Efficient and Easy", PLOS One, 2012, 7(11): 1-6.

Newman et al., "An ultrasensitive method for quantitating circulating tumor DNA with broad patient coverage", Nature Medicine., 2014, 20(5): 548-554.

Schmitt et al., "Detection of ultra-rare mutations by next-generation sequencing", Proceedings of the National Academy of Sciences, 2012, 109(36): 14508-14513.

\* cited by examiner

METHOD FOR BIDIRECTIONAL SEQUENCING

CROSS-REFERENCING

This application is a § 371 national phase of International Application No. PCT/IB2016/055251, filed on Sep. 1, 2016, which claims the benefit of UK patent application serial no. 1515557.5, filed on Sep. 2, 2015, which applications are incorporated by reference herein.

BACKGROUND

Many diseases are caused by somatic mutations. Because somatic mutations only occur in a fraction of the cells in the body, they can be very difficult to detect by next generation sequencing (NGS). One problem is that every library preparation method and sequencing platform results in sequence reads that contain errors, e.g., PCR errors and sequencing errors. While it is sometimes possible to correct systematic errors (e.g., those that are correlated with known parameters including sequencing cycle-number, strand, sequence-context and base substitution probabilities), it is often impossible to figure out with any certainty whether a variation in a sequence is caused by an error or if it is a "real" mutation. This problem is exacerbated if the amount of sample is limited and mutation-containing polynucleotides are present only at relatively low levels, e.g., less than 5%, in the sample. For example, if a sample contains only one copy of a mutation-containing polynucleotide in a background of hundreds of polynucleotides that are otherwise identical to the mutation-containing polynucleotide except that they do not contain the mutation, then, after those polynucleotides have been sequenced, it is often impossible to tell whether the variation (which may only be observed in about 1/100 of the sequence reads) is an error that occurred during amplification or sequencing. Thus, the detection of somatic mutations that cause diseases can be extremely difficult to detect with any certainty.

Schmitt et al (Proc. Natl. Acad. Sci. 2012 109: 14508-14513) proposed a solution that involves tagging a sample with custom Y-shaped adaptors. The Y-shaped adaptors were generated by first introducing a single-stranded randomized nucleotide sequence into the stem region of one adaptor strand. A second adaptor strand, is then extended using a DNA polymerase, to generate a Y-shaped adaptor where the stem region has a complementary double-stranded randomized nucleotide sequence. Adaptors are then tailed by adding a 3' base overhang using a DNA polymerase. The overhang assists in adaptor ligation to fragmented DNA tailed with a complementary base. Adaptors are ligated to fragmented DNA before the library is PCR amplified, using primers that hybridize to the single stranded (non-stem) region of the adaptors. Tag sequences allow reads deriving from the top strands of fragmented DNA to be discriminated from sequence reads derived from bottom strands. This requires paired-end sequencing and comparison of both read 1 and read 2 tag sequences. Schmitt's method is based on the idea that for a true DNA mutation, complementary substitutions should be present on both strands and, as such, a mutation can only be called with confidence if it is present in sequences from both strands.

While useful for discriminating between sequence reads from top and bottom strands, Schmitt's method has several limitations.

First, because sequence tags are random it can be difficult to identify tags that have been 'mutated' due to PCR or sequencing errors. In addition, it is difficult to detect errors that occurred during oligonucleotide synthesis, such as n-1 deletions.

Second, manufacture of the double-stranded adaptors is complex and expensive. Typically, Y-shaped adaptors are manufactured by annealing two oligonucleotides. In contrast, Schmitt's method also includes incorporation of random bases into the oligonucleotide, DNA polymerase extension and tailing different 3' bases onto adaptors and fragmented DNA. These steps can be inefficient and require additional purification and quality control checks.

Third, it is difficult to control the relative incorporation of different bases in the degenerate tag sequence during oligonucleotide synthesis. This can result in some tag sequences being present at higher levels than others in the pool of Y-shaped adaptors, which reduces the probability that a fragment is tagged with unique tag sequences.

Fourth, because the tags are attached to the template in bulk, a number of tag sequences are required to reduce the probability of different fragments being attached to adaptors containing the same tag sequences and to improve the chance of detecting a PCR and/or sequencing error that results in one tag being 'mutated' into another. As a result, the tag sequences are typically relatively long; for example, Schmitt use 12 nucleotide tag sequences. However, long runs of random bases are likely to form intra- and inter-molecular hybrids, which can cause problems for downstream applications such as in-solution hybridization. In this application, adaptor and index sequences are 'masked' to reduce the effect of inter-molecular hybridisation by including blocking oligonucleotides in the hybridization. However, masking the degenerate region of the tag requires incorporation of 'universal' bases such as inosine, with associated additional costs. In addition, tag sequences use up a proportion of each sequencing read thereby reducing the sequence data from target fragment(s). This effect is increased if tag sequences are longer.

Fifth, in the Schmitt protocol the PCR is performed on a pool of molecules, each tagged with different 5' and 3' random tag sequences. Failure to remove residual adaptors can result in hybridization of an adaptor strand to a template molecule during PCR, which can inadvertently tag a molecule with a different tag sequence.

Finally, Schmitt tag DNA fragments with both 5' and 3' random tag sequences. If, by chance, the 5' and 3' tag sequences are complementary, or partially complementary, then the tags can intra-molecularly hybridize resulting in suppression of PCR amplification. This can result in uneven amplification of template molecules, depending on their 5' and 3' tag combination.

The present disclosure provides an alternative, better, way for tagging DNA molecules in a way that the sequence reads from top and bottom strands can be discriminated.

SUMMARY

Described herein is a method of sequencing. In some embodiments the method may comprise: splitting an asymmetrically tagged library into a plurality of subsamples, tagging the adaptor-ligated DNA in the sub-samples with sequence tags that identify the sub-samples, optionally pooling the sub-samples, sequencing polynucleotides from each of the tagged sub-samples, or copies of the same, to produce sequence reads each comprising: (i). a sub-sample identifier sequence and (ii). the sequence of at least part of a fragment in the sample, where at least some of the sequence reads are derived from the top strand of a fragment in the sample and some of the sequence reads of are derived from the bottom strand of the same fragment.

As will be described in greater detail below (and illustrated in FIG. 1), the method provides sequence reads in which sequence reads that are derived from different strands (i.e., the top and bottom strands) of the same fragment (i.e., the same original double-stranded molecule) can be distinguished. In addition, the method provides a way to distinguish sequence reads that are derived from fragments that are otherwise identical. These features allow one to identify sequence variation with exceptional confidence.

The method finds particular use in analyzing samples of DNA in which the amount of DNA, or diversity of fragmentation breakpoints, is limited and/or that contain fragments having a low copy number mutation (e.g. a sequence caused by a mutation that is present at low copy number relative to sequences that do not contain the mutation). These features are often present in patient samples that can be obtained non-invasively, e.g., circulating tumor (ctDNA) samples, which can obtained from peripheral blood, or invasively, e.g., tissue sections. In such samples, the mutant sequences may only be present at a very limited copy number (e.g., less than 10, less than 5 copies or even 1 copy in a background of hundreds or thousands of copies of the wild type sequence) and there is a high probability that at least some of the mutant fragments have an otherwise identical sequence (including identical ends) to a wild type fragment. In these situations, it can be almost impossible to identify a sequence variation with significant confidence.

The present method—because it involves splitting, and tagging, the sample after it is tagged with a "generic" asymmetric adaptor—has multiple advantages over the prior methods, e.g., the Schmitt method summarized above. For example, sequence tags used for each sub-sample can be error-correctable rather than random sequences. Therefore errors in the tag sequences can be recovered, retaining many reads that would otherwise be misassigned or rejected by the analysis pipeline. Second, manufacture of adaptors in the present method is more straightforward than the method used by Schmitt. Adaptors can be manufactured by annealing oligonucleotides thereby avoiding enzymatic steps and subsequent purification and quality controls steps. Third, unlike degenerate oligonucleotide synthesis, non-degenerate oligonucleotides do not have synthesis biases. Fourth, because tag sequences can be designed, rather than random, they can be of specified length and sequence composition. For example, this can allow design of specific blocking sequences, tailoring the length of tags to a specific sequencing platform or avoiding secondary structure(s). Fifth, generic adaptors do not include tag sequence(s) therefore residual adaptor strands cannot inadvertently hybridize to a molecule and add a different tag sequence. Sixth, tag combinations can be rationally designed rather than random combinations of different 5' and 3' random tag sequences. Therefore tag combinations can be chosen to minimize uneven amplification of template molecules.

BRIEF DESCRIPTION OF THE DRAWINGS

The invention is best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. A DNA target may originate from any source such as genomic DNA, or an artificial DNA construct. Any sample containing nucleic acid, e.g., genomic DNA from tissue culture cells or a sample of tissue, may be employed herein.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded or partially double-stranded. If double-stranded, the primer is usually first treated to separate its strands before being used to prepare extension products. This denaturation step is typically effected by heat, but may alternatively be carried out using alkali, followed by neutralization. Also included in this definition are toehold exchange primers, as described in Zhang et al (Nature Chemistry 2012 4: 208-214), which is incorporated by reference herein.

Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand region in a hybridization reaction. The hybridization reaction can be made to be highly specific by adjustment of the hybridization conditions (often referred to as hybridization stringency) under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotide region that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acids, which are produced from the amplifying process as defined herein.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "copies of fragments" refers to the product of amplification, where a copy of a fragment can be a reverse complement of a strand of a fragment, or have the same sequence as a strand of a fragment.

The term "substantially identical sequences" refers to sequence that are at least 95% or at least 99% identical to one another.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "ligating," as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary," they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "extending", as used herein, refers to the extension of a primer by the addition of nucleotides using a polymerase. If a primer that is annealed to a nucleic acid is extended, the nucleic acid acts as a template for extension reaction.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencingby-ligation platforms currently employed by Illumina, Life Technologies, and Roche, etc. Next-generation sequencing methods may also include nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences.

The term "bidirectional sequencing", as used herein, refers to sequencing the top and bottom strands of an initial fragment of double stranded DNA in spatially distinct sequencing reactions, where the top and bottom sequence reads can be paired with each other and compared during data analysis. Paired-end sequencing, on the other hand, is not bidirectional sequencing because, in paired end sequencing, both ends of the sequenced amplicon are derived from only one strand of an initial fragment.

The term "asymmetric adaptor", as used herein, refers to an adaptor that, when ligated to both ends of a double stranded nucleic acid fragment, will lead to a top strand that contains a 5' tag sequence that is not the same as or complementary to the tag sequence at the 3' end. Exemplary asymmetric adapters are described in: U.S. Pat. Nos. 5,712, 126 and 6,372,434 and WO/2009/032167; all of which are incorporated by reference herein in their entirety. An asymmetrically tagged fragment can be amplified by two primers: one that hybridizes to a first tag sequence added to the 3' end of a strand, and another that hybridizes to the complement of a second tag sequence added to the 5' end of a strand. Y-adaptors and hairpin adaptors (which can be cleaved, after ligation, to produce a "Y-adaptor") are examples of asymmetric adaptors.

The term "Y-adaptor" refers to an adaptor that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adaptor-tagged double-stranded DNA that has been ligated to a Y-adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

The term "hairpin adaptor" refers to an adaptor that is in the form of a hairpin. In one embodiment, after ligation the hairpin loop can be cleaved to produce strands that have non-complementary tags on the ends. In some cases, the loop of a hairpin adaptor may contain a uracil residue, and the loop can be cleaved using uracil DNA glycosylase and endonuclease VIII, although other methods are known.

The term "adaptor-ligated sample", as used herein, refers to a sample that has been ligated to an adaptor. As would be understood given the definitions above, a sample that has been ligated to an asymmetric adaptor contains strands that have non-complementary sequences at the 5' and 3' ends.

The term "splitting", as used herein, refers to an action in which two or more portions of an initial sample are separated from one another and, e.g., placed into separate vessels. In some cases, the term "splitting" means that a sample is divided into equal parts. In other cases, the term "splitting" means that a sample is divided into unequal parts. In some cases, the term "splitting" means that several aliquots of an initial sample are removed from one vessel and placed into other vessels, where not all of an initial sample is aliquoted into the other vessels. In these cases, the portion of the initial sample that remains in the original vessel may be used as a sub-sample, as described below.

The term "a plurality of sub-samples", as used herein, refers to the product of a sample that has been split. For example, if two portions of an initial sample are removed from one vessel and placed into two other vessels, then there are two sub-samples.

The term "tagging" as used herein, refers to the appending of a sequence tag (that contains an identifier sequence) onto a nucleic acid molecule. A sequence tag may be added to the 5' end, the 3' end, or both ends of nucleic acid molecule. A sequence tag can be added to a fragment by ligating an oligonucleotide to the fragment. In some cases, ligation to a single stranded end of a nucleic acid may be facilitated by a splint oligonucleotide, where a "splint oligonucleotide" refers to an oligonucleotide that, when hybridized to other polynucleotides, acts as a "splint" to position the polynucleotides next to one another so that they can be ligated together using, e.g., T4 DNA or another ligase. In other embodiments, ligation to a single stranded end of a nucleic acid may be facilitated by a single-strand DNA ligase. A sequence can also be added by primer extension when the primer comprises, at its 3' end, a sequence that binds to a sequence in the fragment and, at its 5' end, the tag sequence.

The terms "identifier sequence" and "tag sequence that identifies" are used interchangeably herein to refer to a sequence of nucleotides used to identify and/or track the source of a polynucleotide in a reaction. After the polynucleotides in a sample are sequenced, the identifier sequence can be used to distinguish the sequence reads and/or determine from which sample a sequence read is derived. An "identifier sequence" may be referred to as a "sample barcode", "index" or "indexer" sequence in other publications. For example, different samples (e.g., polynucleotides derived from different individuals, different tissues or cells, or polynucleotides isolated at different times points), can be tagged with identifier sequences that are different from one another and, after the samples are tagged, they are pooled. After sequencing, the source of a sequence can be tracked back to a particular sample using the identifier sequence. Identifier sequences can be added to a sample by ligation, by primer extension using a tailed primer that contains an identifier sequence in a 5' tail, or using a transposon. An identifier sequence can range in length from 2 to 100 nucleotide bases or more and may include multiple subunits, where each different identifier has a distinct identity and/or order of subunits. A sample identifier sequence may be added to the 5' end of a polynucleotide, the 3' end of a polynucleotide or both the 5' and 3' end of a polynucleotide, for example. In particular embodiments, a barcode sequence may have a length in range of from 1 to 36 nucleotides, e.g., from 6 to 30 nucleotides, or 8 to 20 nucleotides. In certain cases, the molecular identifier sequence may be error-correcting, meaning that even if there is an error (e.g., if the sequence of the molecular barcode is mis-synthesized, mis-read or is distorted by virtue of the various processing steps leading up to the determination of the molecular barcode sequence) then the code can still be interpreted correctly. Descriptions of exemplary error correcting sequences can be found throughout the literature (e.g., US20100323348 and US20090105959, which are both incorporated herein by reference). In some embodiments, an identifier sequence may be of relatively low complexity (e.g., may be composed of a mixture of 4 to 1024 different sequences), although higher complexity identifier sequences can be used in some cases.

The term "sample identifier sequence" is a sequence of nucleotides that is appended to a target polynucleotide, where the sequence identifies the sample (e.g., which individual, which cell, which tissue, or which times points, etc.) from which a sequence read is derived. In use, each sample is tagged with a different sample identifier sequence (e.g., one sequence is appended to each sample, where the different samples are appended to different sequences), and the tagged samples can be pooled. After the samples are sequenced, the sample identifier sequence can be used to identify the source of the sequences.

The term "sub-sample identifier sequence" and "sequence tag that identifies the sub-sample" are used interchangeably herein to refers to a sequence of nucleotides that is appended to a target polynucleotide (for example, by primer extension), where the sequence sub-sample identifier sequence allows one to distinguish between the various sub-samples. (e.g., which of the 2, 4, 6, 8, or 12 or more sub-samples) from which a sequence read is derived. In use, each sub-sample is tagged with a different sub-sample identifier sequence (e.g., one sequence is appended to each sub-sample, where the different sub-samples are appended to different sequences), or combination of sub-sample identifier sequences, and the tagged sub-samples can be optionally pooled. After sequencing, the sub-sample identifier sequences can be used to distinguish between sequences from one sub-sample and sequences from other sub-samples. As would be apparent, if "sequence tags that identify sub-samples" are used, the sequence tag appended to each sub-sample is different.

As used herein, the term "complementary" in the context of sequence reads that are complementary, refers to reads for sequences that, after the sequences have been trimmed to remove adaptor sequences, are substantially complementary to one another and, in some cases, have identical or near identical ends, indicating that the reads are derived from the same initial template molecules.

The term "opposite strands", as used herein, refers to the top and bottom strands, where the strands are complementary to one another.

The term "potential sequence variation", as used herein, refers to a sequence variation, e.g., a substitution, deletion, insertion or rearrangement of one or more nucleotides in one sequence relative to another.

As used herein, the term "correspond to", with reference to a sequence read that corresponds to a particular (e.g., the top or bottom) strand of a fragment, refers to a sequence read derived from that strand or an amplification product thereof.

The term "identical or near-identical sequences", as used herein, refers to near duplicate sequences, as measured by a similarity function, including but not limited to a Hamming distance, Levenshtein distance, Jaccard distance, cosine distance etc. (see, generally, Kemena et al, Bioinformatics 2009 25: 2455-65). The exact threshold depends on the error rate of the sample preparation and sequencing used to perform the analysis, with higher error rates requiring lower thresholds of similarity. In certain cases, substantially identical sequences have at least 98% or at least 99% sequence identity.

The term "fragmentation breakpoint" is intended to refer to the site at which a nucleic acid fragment is joined to an adaptor. Two sequences that have the same fragmentation breakpoints have the same sequences at their ends (excluding any adaptor sequences that have been added to the fragments). Fragments can be generated by random or non-random methods. In analyzing sequence reads, the fragmentation breakpoint may be identified as the boundary between genomic-derived sequence and adaptor derived sequences (including any overhangs in adaptor sequences).

The term "identical or near-identical fragmentation breakpoints", as used herein, refers to two molecules that have the same 5' end, the same 3' end, or the same 5' and 3' ends, where the differences are due to a PCR error, sequencing error, mapping or alignment error or somatic mutation. A fragmentation breakpoint can be determined by removing the adaptor sequence from a sequence read, leaving the sequence of the target. The first nucleotide of the trimmed sequence represents the first nucleotide after the fragmentation breakpoint. In sequencing an amplified sample, two sequence reads that correspond to fragments that have identical or near-identical fragmentation breakpoints can be derived from the same initial fragment. In many cases, 8-30 nucleotides at the end of a trimmed sequence can be compared to the ends of other trimmed sequences to determine if the fragmentation breakpoints are the same or different. In many cases, fragmentation breakpoints can be identified after mapping reads to a reference sequence. After mapping fragmentation breakpoints may be identified using software e.g., Picard MarkDuplicates (available from the Broad Institute), Samtools rmdup (see, e.g., Li et al. Bioinformatics 2009, 25: 2078-2079) and BioBamBam (Tischler et al, Source Code for Biology and Medicine 2014, 9:13).

The term "pooling", as used herein, refers to the combining, e.g., mixing, of two samples such that the molecules within those samples become interspersed with one another in solution.

The term "pooled sample", as used herein, refers to the product of pooling.

The term "target enrichment", as used herein, refers to a method in which selected sequences are separated from other sequences in a sample. This may be done by hybridization to a probe, e.g., hybridizing a biotinylated oligonucleotide to the sample to produce duplexes between the oligonucleotide and the target sequence, immobilizing the duplexes via the biotin group, washing the immobilized duplexes, and then releasing the target sequences from the oligonucleotides. Alternatively, a selected sequence may be enriched by amplifying that sequence, e.g., by PCR using one or more primers that hybridize to a site that is proximal to the target sequence.

The terms "minority variant" and "sequence variation", as used herein, is a variant that is present a frequency of less than 50%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:100 or less, 1:1,000 or less, 1:10,000 or less, 1:100,000 or less or 1:1,000,000 or less.

The term "sequence diversity", as used herein, refers to the number of 5' and/or 3' breakpoints that are associated with a plurality of fragments corresponding to a target sequence.

Other definitions of terms may appear throughout the specification.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* 3$^{rd}$ Ed., W. H. Freeman Pub., New York, N.Y. and Berg et al. (2002) *Biochemistry*, 5$^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
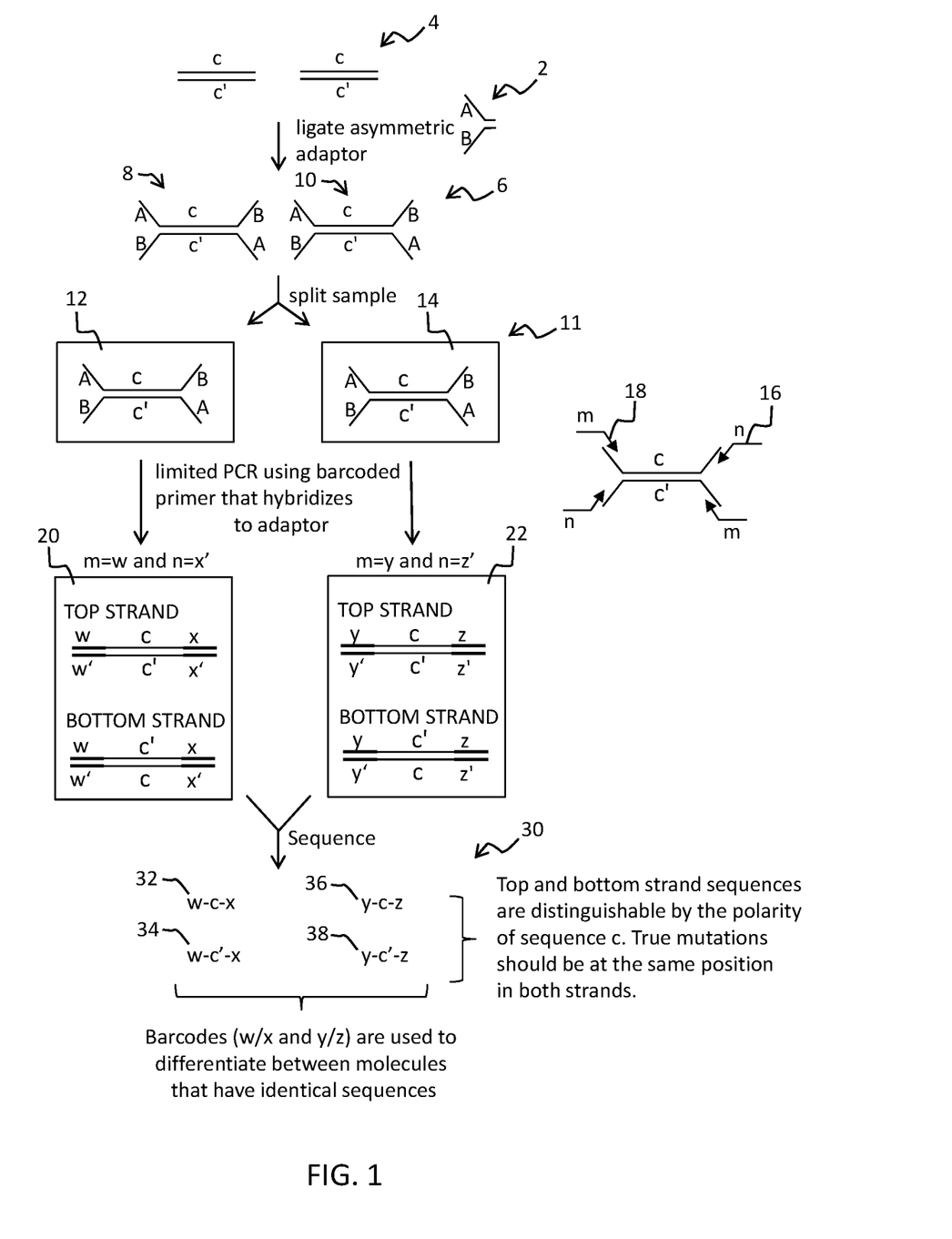
FIG. 1 schematically illustrates some of the principles of the present method.

Some of the principles of the method are shown in FIG. 1. With reference to FIG. 1, the method can be initiated by ligating an asymmetric adaptor 2 to a sample that comprises fragments of DNA 4, to produce an adaptor-ligated sample 6. As shown, asymmetric adaptor 2 can be a Y adaptor, although other types of asymmetric adaptors (e.g., a hairpin adaptor) can also be used. Adaptor-ligated sample 6 contains asymmetrically-tagged fragments 8 and 10, meaning that for each strand, the 5' end tag (A) contains a sequence that is different and not complementary to the sequence of the 3' end tag (B). As would be understood, depending on the sample, this step may be done by repairing the ends of the fragments in the sample, adding an "A" overhang, and then ligating the end-repaired fragments to an asymmetric adaptor that contains a "T" overhang, although other methods can be used. Next, the method comprises splitting the adaptor-ligated sample into a plurality of sub-samples 11. In this step, the adaptor-ligated sample may be split into as many samples as necessary. However, in many embodiments, the adaptor-ligated sample is split into 4 to 96 different sub-samples, e.g., 4 to 16 different sub-samples. As would be readily apparent, this step may be done by removing several aliquots of the adaptor-ligated sample and placing the aliquots in to separate containers.

Next, the method comprises separately tagging the adaptor-ligated DNA in the sub-samples with sequence tags that identify the sub-samples. In some embodiments, this may be done by ligation (e.g., using a splint oligonucleotide or a single-stranded ligase to facilitate ligation) or by primer extension. In some embodiments (and as illustrated in FIG. 1), the tagging may be done by amplifying the adaptor-ligated DNA in each of the sub-samples using primers that hybridize to sequences in the asymmetric adaptor (primers 16 and 18), wherein at least one of the primers has an identifier sequence, and the identifier sequence or, if two primers have identifier sequences, the combination of identifier sequences, can uniquely identify a sub-sample, to produce a tagged product, e.g., an amplification product for each sub-sample (20 and 22). As shown, both primers 16 and 18 have a sub-sample identifier sequence in their 5' tail, where sub-sample identifier sequence m can be any suitable sequence that is unique for each sub-sample, and sequence n can be any suitable sequence that is unique for each sub-sample. Such primers contain a 5' tail that contains the sub-sample identifier sequence and a 3' end that hybridizes to the adaptor added to the fragments and is extended using the fragments as a template, thereby producing a copy of the fragments. Using this method, the copied fragments will contain the molecular barcode at the 5' end. For example, in primer 16, sub-sample identifier sequence m can be w or y and, in primer 18, sub-sample identifier sequence n can be x' (i.e., the complement of x) or z' (i.e., the complement of z). The method will still work if only one of the primers has a sub-sample identifier sequence. The primer extension method shown in FIG. 1 can be readily adapted to ligation-based methods, e.g., by ligating on oligonucleotides that contain sub-sample identifiers, as discussed above, and amplifying the ligation products (which could be pooled together immediately after the ligation reaction) using generic primers to obtain a similar set of amplification products. Alternatively, the nucleic acid in each sub-sample could be amplified by PCR, and the PCR products of sub-sample could be ligated to a sub-sample identifier.

This tagging step can be done by PCR, using a limited number of cycles (e.g., 4 to 20 cycles), to produce tagged products 20 and 22. As shown, subsample 12 is amplified using primers having tails of sequences w and x', and subsample 14 is amplified using primers having tails of sequences y and z'. In tagged sub-sample 20, products derived from the top strand of the molecules in sample 12 will have a top strand of formula w-C-x, and tagged sub-samples derived from the bottom strand of the molecules in sample 12 will have a bottom strand of formula w-C'-x (where C' is the reverse complement of C). Likewise, in tagged sub-sample 22, tagged products derived from the top strand of the molecules in sample 14 will have a top strand of formula y-C-z, and tagged sub-sample products derived from the bottom strand of the molecules in sample 14 will have a bottom strand of formula y-C'-z. As would be apparent, in the sets of tagged sub-samples 20 and 22, the top and bottom strand sequences are distinguishable. For example, in tagged sub-sample 20, the top strand products are of formula w-C-x, whereas the bottom strand products are of formula w-C'-x, which allows the top strand products to be distinguishable from the bottom strand products after sequencing. Likewise, in tagged sub-sample 22, the top strand products are of formula y-C-z, whereas the bottom strand products are of formula y-C'-z, which allows the top strand products to be distinguishable from the bottom strand products after sequencing.

Next, after an optional pooling step in which the tagged sub-samples 20 and 22 can be pooled together, the method comprises sequencing polynucleotides from each of the tagged sub-samples, or copies of the same (if those sequences are amplified), to produce sequence reads 30 each comprising: (i). a sub-sample identifier sequence (w, x, y or z or their complements) and (ii). the sequence of at least part of a fragment in the sample (c or c'). As shown, some of the sequence reads are derived from the top strand of a fragment in the sample and some of the sequence reads are derived from the bottom strand of the same fragment. In other words, at least some of the sequence reads, excluding the sub-sample identifier sequences, are substantially complementary (i.e., some of the sequence reads contain sequence c and some sequence reads contain sequence c') and correspond to opposite strands (i.e., the top and bottom strands) of a fragment in the sample of (a). In the illustrative example shown in in FIG. 1, two identical fragments in sample 4 would result in four types of sequence reads 32, 34, 36 and 38. In these reads, identical or near identical sequence reads derived from different starting molecules in sample 4 can be distinguished by their identifiers (i.e., whether the reads contain sub-sample identifiers w and x or identifiers y and z), and, for sequence reads that contain the same sub-sample identifiers, the strand from which the sequence read is derived (i.e., whether a read is derived from the top strand or the bottom strand of a fragment in sample 4) can be determined by the polarity of the sequence corresponding to that fragment (i.e., whether the sequence is sequence c or it's complement c'). True mutations should be at the same positions in both strands and, as such, if the same mutation is seen in a bottom strand sequence (e.g., w-c-x) as well as a top strand sequence (e.g., w-c'-x), then a sequence variation is more likely to be true. If a mutation is caused by a PCR or a sequencing error, then it is very unlikely to appear at the same place in both strands.

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

The sequence reads may be analyzed by a computer and, as such, instructions for performing the steps set forth below may be set forth as programing that may be recorded in a suitable physical computer readable storage medium. The general principles of some of the analysis steps are described below.

The sequence reads may be processed and grouped in any convenient way. In some embodiments, the sequence reads may be grouped by their sub-sample identifier (e.g., whether they contain identifier w or identifier y), and, optionally, by one or more of the fragmentation breakpoints of the sequence read, where a fragmentation breakpoint is represented by the "end" of the sequence after the tags have been trimmed off (i.e., one or more ends of sequence c or c'). Assuming fragmentation is random, or semi-random, different fragments having the same sequence in sample 4 can be distinguished by their fragmentation breakpoints and, as such, grouping the sequence reads by their fragmentation breakpoints provides a way to determine if a particular sequence (e.g., a sequence variant) is present in more than one starting molecule. In some implementations, initial processing of the sequence reads may include identification of molecular barcodes (including sample identifier sequences or sub-sample identifier sequences), and/or trimming reads to remove low quality or adaptor sequences. In addition, quality assessment metrics can be run to ensure that the dataset is of an acceptable quality.

In certain embodiments, the method may further comprise identifying a potential sequence variation in a group of sequence reads that correspond to the top strand of a fragment and determining if the potential sequence variation is in any of the sequence reads that correspond to the bottom strand of the fragment. As noted above, the confidence that a potential sequence variation is a true variation (rather than a PCR or sequencing error) increases if it is present in both strands of the same molecule in sample 4.

In some embodiments, the method may further comprise identifying identical or near-identical sequence reads that have identical or near-identical fragmentation breakpoints but different sub-sample identifier sequences. In these embodiments, sequence reads derived from two fragments that are otherwise near identical in sequence and fragmentation breakpoints can be distinguished by their sub-sample identifier sequence. As would be apparent, the confidence that a potential sequence variation is a true variation (rather than a PCR or sequencing error) increases if it is present in more than one molecule in sample 4.

The ability to distinguish between: a) sequence reads that are derived from different fragments and b) sequence reads that are derived from different strands of the same fragment allows one to determine whether a sequence variation is real with more confidence.

As alluded to above, in some embodiments, the method may comprise pooling the tagged products prior to the sequencing step to produce a pooled sample. The pool can be an equi-molar or equi-volume mix of different amplified sub-samples, alternatively. However, in some embodiments, different tagged sub-samples can be mixed at different ratios or volumes. In these embodiments, the sequencing step comprises sequencing nucleic acids in the pooled sample. Alternatively, the amplification products may sequenced without pooling. In these embodiments, they may be separately applied to the sequencing substrate and sequenced in the same sequencing run, or sequenced in separate sequencing runs.

In some embodiments, the nucleic acids sequenced in the sequencing step are enriched from the tagged samples by target enrichment, many methods for which are known. In some embodiments, the enrichment may be done by hybridization to a probe, e.g., by SURESELECT™, which may involve hybridizing the amplification products to an oligonucleotide (e.g., RNA) probe that contains an affinity tag (e.g., biotin) to the amplification products. The resultant duplexes can be separated from other molecules' products by binding the oligonucleotide to a solid support and washing, and the target molecules can be released. As would be apparent, such methods may use at least two oligonucleotide probes: for example, probes that target each strand. In some embodiments, however, the enrichment step may be done using probe that hybridize to only one of the strands (e.g., a probe that hybridizes to either the top strand sequence c or bottom strand sequence c'). In these embodiments and with reference to FIG. 1, capturing only one strand of the tagged products using a probe that hybridizes c will enrich for products derived from the top strand of molecule 8 (of sequence w-c-x; 5' to 3') as well as products that are derived from the bottom strand of the same molecule (of sequence x'-c-w'; 5' to 3'), which can be distinguished from one another after sequencing by the orientation of c relative to w and x and their complements. Target enrichment can also be done using target-specific primers by PCR amplification (see, e.g., US20130231253). In some instances, target enrichment may be done in a single reaction or, in some cases, two reactions (one for each strand). In other cases, target enrichment may be done in the same reaction if the probes/primers are not overlapping.

In some embodiments, sample identifiers (i.e., a sequence that identifies the sample to which the sequence is added, which can identify the patient, or a tissue, etc.) can be added to the polynucleotides prior to sequencing, so that multiple (e.g., at least 2, at least 4, at least 8, at least 16, at least 48, at least 96 or more) samples can be multiplexed. In these embodiments, the sample identifier ligated may be to the initial polynucleotides as part of the asymmetric adaptor, or the sample identifier may be ligated to the polynucleotides in the sub-samples, before or after amplification of those polynucleotides. Alternatively, the tag may be added by primer extension, i.e., using a primer that has a 3' end that hybridizes to an adaptor (e.g., the asymmetric adaptor or a tag sequence added to the sub-samples), and a 5' tail that contains the sample identifier. For example, in some embodiments, the asymmetric adaptor may comprise a sample identifier sequence that identifies the sample to which the asymmetric adaptor is added, wherein the amplification products each comprise a sub-sample identifier sequence and a sample identifier sequence, and wherein said sequencing reads comprise the sample identifier sequence and the sub-sample identifier sequence.

The method described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In some embodiments, the sample comprises fragments of human genomic DNA. In some embodiments, the sample may be obtained from a cancer patient. In some embodiments, the sample may be made by extracting fragmented DNA from a patient sample, e.g., a formalin-fixed paraffin embedded tissue sample. In some embodiments, the patient sample may be a sample of cell-free "circulating" DNA from a bodily fluid, e.g., peripheral blood e.g. from the blood of a patient or of a pregnant female. The DNA fragments used in the initial step of the method should be non-amplified DNA that has not been denatured beforehand.

The DNA in the initial sample may be made by extracting genomic DNA from a biological sample, and then fragmenting it. In these embodiments, the initial steps may be mediated by a transposase (see, e.g., Caruccio, Methods Mol. Biol. 2011; 733:241-55), in which case the fragmentation and tagging steps may be done simultaneously, i.e., in the same reaction using a process that is often referred to as "tagmentation". In other embodiments, the fragmenting may be done mechanically (e.g., by sonication, nebulization, or shearing) or using a double stranded DNA "dsDNA" fragmentase enzyme (New England Biolabs, Ipswich Mass.). In some of these methods (e.g., the mechanical and fragmentase methods), after the DNA is fragmented, the ends are polished and A-tailed prior to ligation to the adaptor. Alternatively, the ends may be polished and ligated to adaptors in a blunt-end ligation reaction. In other embodiments, the DNA in the initial sample may already be fragmented (e.g., as is the case for FPET samples and circulating cell-free DNA (cfDNA), e.g., ctDNA). The fragments in the initial sample may have a median size that is below 1 kb (e.g., in the range of 50 bp to 500 bp, or 80 bp to 400 bp), although fragments having a median size outside of this range may be used.

In some embodiments, the amount of DNA in a sample may be limiting. For example, the initial sample of fragmented DNA may contain less than 200 ng of fragmented human DNA, e.g., 10 pg to 200 ng, 100 pg to 200 ng, 1 ng to 200 ng or 5 ng to 50 ng, or less than 10,000 (e.g., less than 5,000, less than 1,000, less than 500, less than 100 or less than 10) haploid genome equivalents, depending on the genome.

Bioinformatics Workflow

Figure 4:
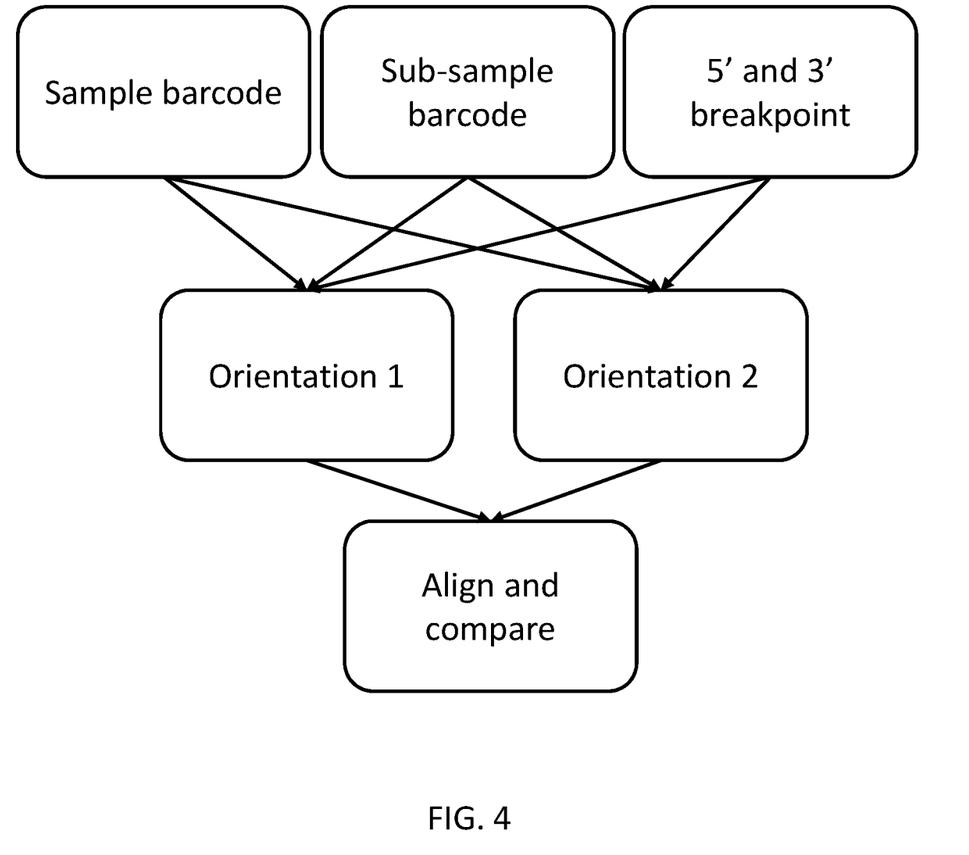
FIG. 4 shows a flow chart illustrating a bioinformatics workflow.

In some embodiments, wherein sequence reads that have near identical fragmentation breakpoints, the same sub-sample identifier and those that are substantially identical are grouped into "read groups". Fragments with the same fragmentation breakpoints have substantially identical sequences at positions adjacent to the adaptor. These can be identified, e.g., in paired-end reads as substantially identical 5' sequences from both read 1 and read 2. Similarly, single-end reads that traverse both breakpoints can be used to identify sequences adjacent to both adaptor sequences. In some embodiments, reads are trimmed to remove adaptor sequences, overhang sequences for ligation and the like. For example, all of the sequence reads in a read group may have a contiguous sequence of at least 10, 15, 20 or 30 nucleotides at the 5' end that are substantially identical to one another and a contiguous sequence of at least 10, 15, 20 or 30 nucleotides at the 3' end that are substantially identical to one another. One way a bioinformatics workflow can be implemented is shown in FIG. 4. In this workflow, reads with the same sample barcode, sub-sample barcode and 5' and 3' breakpoint are grouped. Reads are then divided on whether they are in orientation 1 or orientation 2 relative to read1/read2 (i.e. A-c-B vs A'-c-B'). Sequences from orientation 1 and 2 are then compared. Genuine variants are expected to be present in molecules from orientation 1 AND 2. PCR or NGS errors are only expected in orientation 1 OR 2. In some cases, the read groups that do not contain reads from both strands of the original fragment are discarded. In other embodiments, the read groups that do not contain reads from both strands of the original fragment are retained, but the sequence is given a lower probability of being correct. In some cases, an error model derived from corrected reads can be applied to these groups.

The informatics steps of the above-described method can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In certain embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

In any embodiment, data can be forwarded to a "remote location," where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standard programming techniques to conduct the various assigning, calculating, identifying, scoring, accessing, generating or discarding steps.

The following patent publications are incorporated by reference for all purposes, particularly for methods by which nucleic acid molecules may be manipulated, reagents for doing the same, for sequencing library preparation workflow, sequencing methods, data processing methods, and for definitions of certain terms: U.S. Pat. No. 8,481,292, WO2013128281, and Casbon (Nuc. Acids Res. 2011, 22 e81), US20150044678, US20120122737, U.S. Pat. No. 8,476,018 and all references cited above and below.

Kits

Also provided by this disclosure is a kit for practicing the subject method, as described above. A subject kit may contain at least: a) an asymmetric adaptor; and b) a plurality (e.g., at least 4-96 or more) of pairs of primers, wherein both primers in each pair comprise a 3' end that is the same as or complementary to a sequence in the adaptor and wherein at least one of the primers in each pair comprises a barcode of, e.g., 2-30 nucleotides in its 5' tail that distinguishes that primer from other primers. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

As would be readily apparent, the method described above may be employed to analyze any type of sample, including, but not limited to samples that contain heritable mutations, samples that contain somatic mutations, samples from mosaic individuals, pregnant females (in which some of the sample contains DNA from a developing fetus), and samples that contain a mixture of DNA from different sources. In certain embodiments, the method may be used identify a minority variant that, in some cases, may be due to a somatic mutation in a person.

In some embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which may be associated with breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma (see, e.g., Chial 2008 Proto-oncogenes to oncogenes to cancer. Nature Education 1:1). Other oncogenic mutations (which may be somatic mutations) of interest include mutations in, e.g., APC, AXIN2, CDH1, GPC3, CYLD, EXT1, EXT2, PTCH, SUFU, FH, SDHB, SDHC, SDHD, VHL, TP53, WT1, STK11/LKB1, PTEN, TSC1, TSC2, CDKN2A, CDK4, RB1, NF1, BMPR1A, MEN1, SMAD4, BHD, HRPT2, NF2, MUTYH, ATM, BLM, BRCA1, BRCA2, FANCA, FANCC, FANCD2, FANCE, FANCF, FANCG, NBS1, RECQL4, WRN, MSH2, MLH1, MSH6, PMS2, XPA, XPC, ERCC2-5, DDB2 or MET, which may be associated with colon, thyroid, parathyroid, pituitary, islet cell, stomach, intestinal, embryonal, bone, renal, breast, brain, ovarian, pancreatic, uterine, eye, hair follicle, blood or uterus cancers, pilotrichomas, medulloblastomas, leiomyomas, paragangliomas, pheochromocytomas, hamartomas, gliomas, fibromas, neuromas, lymphomas or melanomas. In some embodiments, the method may be employed to detect a somatic mutation in genes that are implicated in cancer, e.g., CTNNB1, BCL2, TNFRSF6/FAS, BAX, FBXW7/CDC4, GLI, HPVE6, MDM2, NOTCH1, AKT2, FOXO1A, FOXO3A, CCND1, HPVE7, TAL1, TFE3, ABL1, ALK, EPHB2, FES, FGFR2, FLT3, FLT4, KRAS2, NTRK1, NTRK3, PDGFB, PDGFRB, EWSR1, RUNX1, SMAD2, TGFBR1, TGFBR2, BCL6, EVI1, HMGA2, HOXA9, HOXA11, HOXA13, HOXC13, HOXD11, HOXD13, HOX11, HOX11L2, MAP2K4, MLL, MYC, MYCN, MYCL1, PTNP1, PTNP11, RARA, SS18 (see, e.g., Vogelstein and Kinzler 2004 Cancer genes and the pathways they control. Nature Medicine 10:789-799). The method of embodiment may be employed to detect any somatic mutation that is implicated in cancer which is catalogued by COSMIC (Catalogue of Somatic Mutations in Cancer), data of which can be accessed on the internet.

Other mutations of interest include mutations in, e.g., ARID1A, ARID1B, SMARCA4, SMARCB1, SMARCE1, AKT1, ACTB/ACTG1, CHD7, ANKRD11, SETBP1, MLL2, ASXL1, which may be at least associated with rare syndromes such as Coffin-Siris syndrome, Proteus syndrome, Baraitser-Winter syndrome, CHARGE syndrome, KBG syndrome, Schinzel-Giedion syndrome, Kabuki syndrome or Bohring-Opitz syndrome (see, e.g., Veltman and Brunner 2012 De novo mutations in human genetic disease. Nature Reviews Genetics 13:565-575). Hence, the method may be employed to detect a mutation in those genes.

In other embodiments, the method may be employed to detect a mutation in genes that are implicated in a variety of neurodevelopmental disorders, e.g., KAT6B, THRA, EZH2, SRCAP, CSF1R, TRPV3, DNMT1, EFTUD2, SMAD4, LIST, DCX, which may be associated with Ohdo syndrome, hypothyroidism, Genitopatellar syndrome, Weaver syndrome, Floating-Harbor syndrome, hereditary diffuse leukoencephalopathy with spheroids, Olmsted syndrome, ADCA-DN (autosomal-dominant cerebellar ataxia, deafness and narcolepsy), mandibulofacial dysostosis with microcephaly or Myhre syndrome (see, e.g., Ku et al 2012 A new paradigm emerges from study of de novo mutations in the context of neurodevelopmental disease. Molecular Psychiatry 18:141-153). The method may also be employed to detect a somatic mutation in genes that are implicated in a variety of neurological and neurodegenerative disorders, e.g., SCN1A, MECP2, IKBKG/NEMO or PRNP (see, e.g., Poduri et al 2014 Somatic mutation, genetic variation, and neurological disease. Science 341(6141):1237758).

In some embodiments, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may be the same location as the first location), where it may be interpreted by a health professional (e.g., a clinician, a laboratory technician, or a physician such as an oncologist, surgeon, pathologist or virologist), as part of a clinical decision.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

Theoretical Background

Different library preparation methods and NGS chemistries have their own systematic error profiles. It is possible to correct systematic errors, in part at least, that are correlated with known parameters including sequencing cycle-number, strand, sequence-context and base substitution probabilities (Meacham et al BMC Bioinformatics. 2011 12: 451). Random errors can be mitigated by replicate sequencing. However, neither method is sufficient if attempting to detect, with high specificity, a minority variant with frequency of ≤~3%. To improve error-detection and correction, several groups have used a repeat-code approach. The idea is to sequence copies of the same molecule. The copies are then aligned and a majority-vote used to generate a consensus sequence, which removes most of the errors. In addition, differences between each copy and the consensus sequences can be used to build up an error-model of a specific genomic region, which can then be applied to clean-up consensus sequences. For example, see Shugay et al 2014 (Towards error-free profiling of immune repertoires. Nature Methods 11, 653-655 (2014)).

Four main methods can be applied to identify copies of the same molecule: (1) fragmentation breakpoints; (2) orientation of a DNA insert compared to surrounding adaptor sequences; (3) DNA barcodes and (4) physical separation.

If, by chance, two molecules have the same 5' and 3' breakpoints then we might incorrectly group reads and attempt to generate a consensus sequence. This could result in a false negative if a variant base was not called as part of the consensus sequence (e.g. if there were a greater number of, or higher quality, reads including a non-variant base). Additionally, our error model could be tricked into assuming that a variant base position was error-prone when in fact genuine calls are mixed from two, or more, different molecules. To mitigate this effect Newman et al (2014) classified unique molecules as those with unique 5' and 3' breakpoints and 100% sequence identity, ignoring low quality base calls. This reduces false negative variants but is likely to increase false-positive calls owing to grouping of reads with errors. Newman et al (2012) appear aware of this deficiency as they discuss implementing molecular tagging approaches to improve data quality.

Cell-free or circulating tumour DNA (ctDNA) is tumour DNA circulating freely in the blood of a cancer patient. Protocols to extract ctDNA generally aim to reduce contamination with normal DNA from leukocytes. This is achieved by rapid processing of whole blood by centrifugation to remove all cells, and analysis of the remaining plasma. ctDNA is highly fragmented, with a mean fragment size ~165 bp. Newman et al (Nat Med. 2014 20: 548-54) made libraries from 7-32 ng ctDNA isolated from 1-5 mL plasma. This is equivalent to 2,121-9,697 haploid genomes (assuming 3.3 pg per haploid genome). This range represents the maximum number of unique molecules that can be captured and sequenced. In practice the maximum number of molecules that can be captured is reduced by random fragmentation of regions covered by bait targets and inefficiencies during library preparation and target recovery.

To estimate the frequency of molecules with identical 5' and 3' breakpoints, one can make several simplifying assumptions: (1) breakpoints are randomly distributed; (2) to be captured a fragment must have 100% match to an RNA bait; and (3) that the library has a fixed sized range between 120-165 bp. For example, imagine a fragment where a 5' breakpoint maps 25 bp upstream of the RNA bait. To be within the fixed library size range the 5' breakpoint could be associated with any of 20 different 3' breakpoints. The same calculation can be performed for each of the possible 5' and 3' breakpoints that generate fragments within the size range. The total number of breakpoints can be calculated using: $\Sigma_{d=0}^{45} d+1$ where d is the difference in length between the maximum fragment length and the RNA bait length. In the above example, d=45 giving 1,081 breakpoints. Next, we can estimate the number of duplicate molecules using collision theory. The expected total number of times a selection will repeat a previous selection as x integers are chosen from a list of y integers (1, y) equals:

$$x - y + y\left(\frac{y-1}{y}\right)^x.$$

In our case, this can be paraphrased as the expected total number of times a captured molecule x will have the same two breakpoints as another captured molecule, where y is the number of molecules with different breakpoints in the library. For example, if x=1,000 and y=1,081 then 347 captured molecules are expected to have the same breakpoints as another captured molecule. In practice, the number of molecules that cannot be uniquely identified is likely higher than 347 because some of the 1,081 breakpoint combinations are likely to be observed more often than others, owing to the distribution of fragment sizes around a mean length and biases in fragmentation breakpoints. This suggests that one needs information in addition to the fragmentation breakpoints in order to uniquely identify molecules for error-correction.

Figure 3:
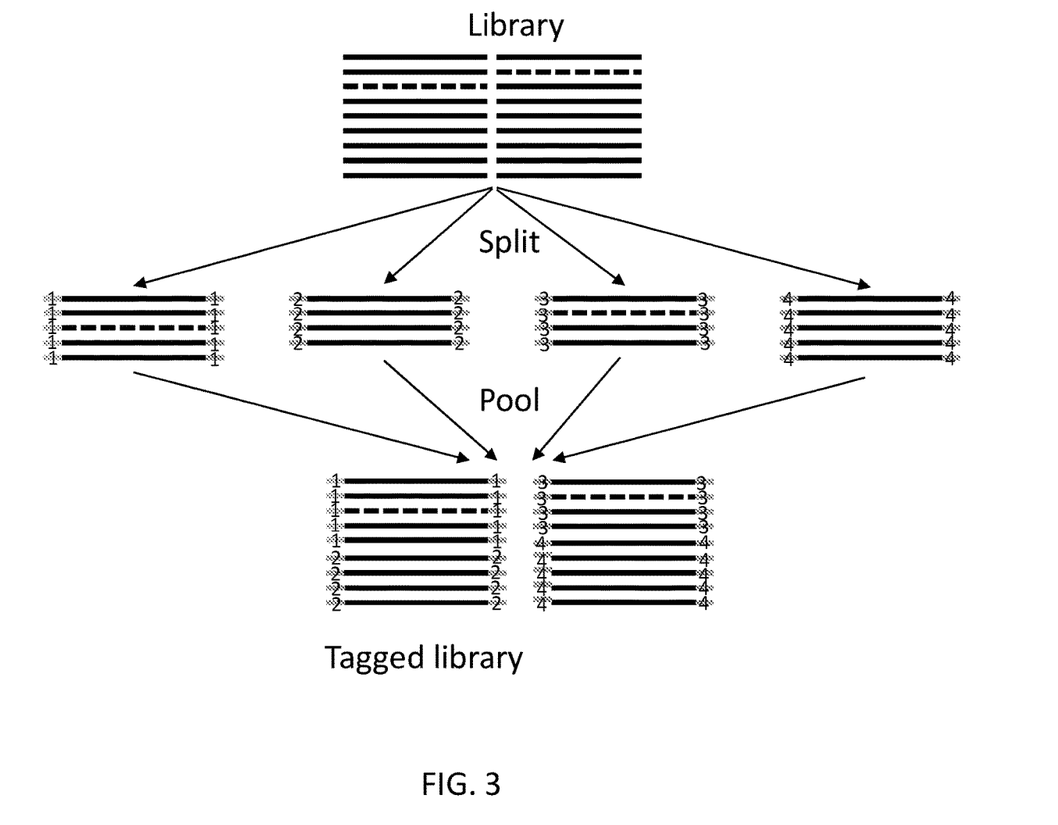
FIG. 3 illustrates a split-pool method. Two double-stranded library molecules, indicated by dashed lines, have the same 5' and 3' breakpoints. The library is split between multiple labelling reactions (barcodes 1, 2, 3 and 4 at the 5' and 3' ends of library molecules). Labelled reactions are then pooled. The two dashed line library molecules are associated with different barcodes so, even though they have the same 5' and 3' breakpoints, individual molecules can be identified.

DNA barcodes can be used on their own, or in addition with fragmentation breakpoints, to help identify duplicate molecules. There is an important distinction between methods where a pool of DNA barcodes, with different sequences, is attached en masse and split-pool methods where individual DNA barcodes are attached in separate reactions before pooling. If barcodes are attached en masse, they are added to template DNA before amplification (and if they are attached en masse by extension of a barcoded primer, great care must be taken to ensure that residual unextended primers are removed before amplification). These restrictions are not necessary if using a split-pool method, where sub-sample barcodes can be added before, during, or after, amplification. In addition, en masse tagging usually requires that the pool of barcode sequences are carefully pooled before tagging. If barcodes are pooled from individual synthesis reactions then care must be taken not to over- or under-represent individual barcode sequences. Alternatively, if barcodes are degenerate then there can be bias. This restriction does not occur in split-pool methods where each sub-sample is associated with one, or a pair, of barcode sequences. FIG. 3 shows a split-pool method.

How many separate sub-samples are required? This depends on the probability that two, or more, fragments in the initial library have the same 5' and 3' breakpoints. In the earlier worked example, the expected total number of times a captured molecule x will have the same breakpoint as another captured molecule, where y is the number of molecules with different breakpoints in the library equaled 347, where x=1000 and y=1,081. If we split the reaction over eight sub-samples then x=125 (1000/8) molecules per sub-sample. We can then use the collision formula with x=125 and y=1,081 to estimate that in each sub-sample ~7 tagged molecules are expected to have the same breakpoint, and barcode sequence, as another molecule. If we pool molecules from each sub-sample into a single pool then 56 (7*8) molecules are expected to have the same breakpoint, and barcode sequence, as another molecule. This is approximately a ~6-fold (347/56) reduction in duplicates than if we did not split, tag and pool. Similarly, if we use 16 wells then x=63 (1000/16), y=1,081 and the estimated number of duplicates is ~2, an approximately ~174-fold (347/2) reduction in duplicates. This suggests that separate reactions can be set up in a 96-well plate, rather than requiring specialist microfluidics.

Physical separation methods include clonal amplification in a microdroplet or on a solid-surface (e.g. an Illumina flow-cell). Microdroplet methods generally rely on limiting dilution of template where each microdroplet contains only a fraction of the total genome (digital PCR, RainDance Technologies' Thunderstorm platform for target enrichment or 10× Genomics GemCode system). However, current physical methods require complex microfluidics.

Example 1

Figure 2:
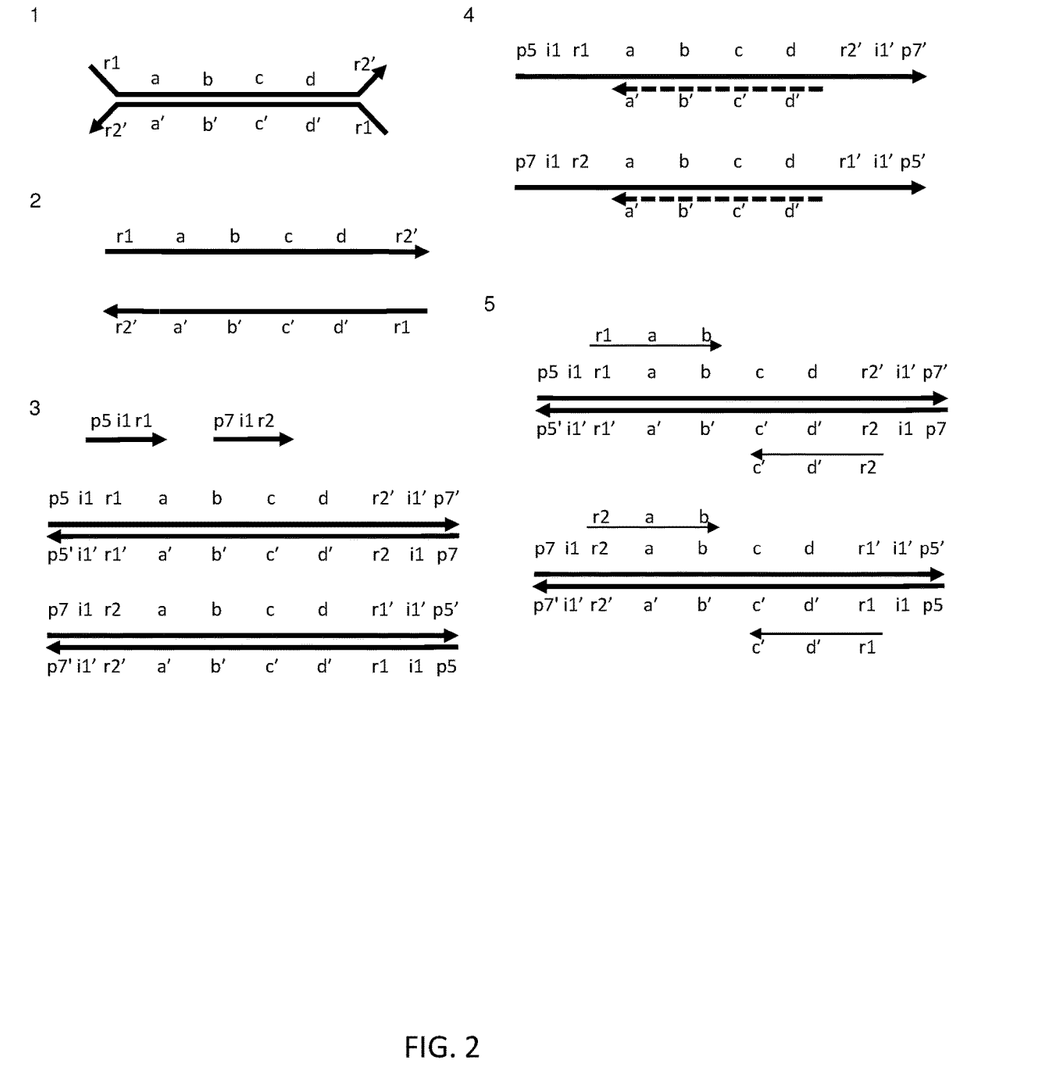
FIG. 2 overview of workflow of one implementation of the present method. (P5 and P7 are Illumina flow cell sequences. i1 is index 1. R1 and R2 are read 1 and read 2 sequences. Prime indicates a sequence is reverse complemented. The 3' end of a strand is indicated by an arrow. a, b, c, d represent regions of a genomic fragment.

If double-stranded DNA is tagged with Y-shaped asymmetric adaptors then each strand has a different insert orientation relative to read 1 and 2 adaptor sequences (FIG. 2). Hybridization capture using Agilent SureSelect is specific to one strand. If a non-amplified library is captured then sequencing data derives from only one of the two strands. To derive sequencing data from both strands, a single primer-extension or PCR step is used before capture (see FIG. 2).

In one embodiment, ctDNA is end-repaired, 3' adenylated and ligated to generic Y-shaped adaptors. In the Agilent SureSelect$^{XT2}$ Target Enrichment System for Illumina Paired-End Multiplex Sequencing protocol, 5-8 cycles of PCR are used to bulk amplify the library. Adaptors, or PCR primers, include sample-specific barcodes for multiplexing prior to hybridization capture. Instead, in the approach described here, one library is split into multiple separate PCR reactions or sub-samples. Each PCR reaction is labelled with barcode(s) using one, or both, primers. After PCR, the separate reactions are pooled together and used as template in a hybridization capture. After capture, and washing, libraries are bulk PCR amplified before paired-end NGS. Fragments are identified using 5' and 3' breakpoints in addition to barcode sequence(s) (see FIGS. 2 and 3).

Example 2

In a second embodiment, ctDNA is end-repaired, 3' adenylated and ligated to generic Y-shaped adaptors. The library is split into multiple separate reactions. In each reaction the library is amplified by PCR using generic PCR primers. After amplification, barcodes are ligated to the PCR amplicons. After ligation, the separate reactions are pooled together and used as template in a hybridization capture. After capture, and washing, libraries are bulk PCR amplified before paired-end NGS. Fragments are identified using 5' and 3' breakpoints in addition to barcode sequence(s) (see FIGS. 2 and 3).

That which is claimed is:

1. A method for determining if a potential sequence variation is in the top and bottom strands of the same DNA fragment, comprising:
   (a) ligating an asymmetric adaptor to a sample that comprises fragments of DNA, to produce an adaptor-ligated sample, wherein the fragments of DNA in the sample have a median size in the range of 80 bp to 400 bp;
   (b) splitting the adaptor-ligated sample into a plurality of sub-samples, wherein each of the sub-samples is placed in one container and the different sub-samples are placed in separate containers;
   (c) separately tagging each of the different sub-samples with one of a plurality of sequence tags that identify the different sub-samples of step (b) by polymerase chain reaction (PCR) using primers that have a 5' tail that has a sub-sample identifier sequence, wherein the 5' tail does not hybridize to the adaptor-ligated sample, to produce tagged sub-samples;
   (d) sequencing polynucleotides from each of the tagged sub-samples of step (c), or copies of the same, to produce sequence reads, each of the sequence reads comprising: (i) one of the plurality of sequence tags that identify the different sub- samples and (ii) the sequence of at least part of a fragment from one of the sub-samples,
      wherein some of the sequence reads of step (d) are derived from the top strand of the fragment from one of the subsamples and some of the sequence reads of step (d) are derived from the bottom strand of the same fragment;
   (e) identifying a potential sequence variation in a group of the sequence reads of step (d), wherein the group of sequence reads corresponds to the top strand of the fragment from one of the sub-samples; and
   (f) determining if the potential sequence variation is in a group of the sequence reads of step (d) that corresponds to the bottom strand of the same fragment.

2. The method of claim 1, wherein the method comprises grouping the sequence reads of step (d), wherein sequence reads that have identical [or near-identical] sequences, identical [or near-identical] fragmentation breakpoints and the same sub-sample identifier sequence are placed in a group.

3. The method of claim 1, wherein the method comprises: pooling the tagged sub-samples of step (c) prior to step (d) to produce a pooled sample, and wherein step (d) comprises sequencing nucleic acids in the pooled sample.

4. The method of claim 1, wherein the polynucleotides sequenced in (d) are selected by target enrichment.

5. The method of claim 4, wherein the target enrichment is done by polymerase chain reaction.

6. The method of claim 1, wherein the asymmetric adaptor is a Y adaptor.

7. The method of claim 1, wherein the asymmetric adaptor comprises a sample identifier sequence that identifies the sample to which the asymmetric adaptor is added, wherein the polynucleotides from each of the tagged sub-samples each comprise one of the sequence tags that identify the sub-samples and the sample identifier sequence, and wherein the sequencing reads of step (d) further comprise the sample identifier sequence.

8. The method of claim 1, wherein one or more of the sequence tags used in step (c) contain a sample identifier sequence that identifies the sample of step (a), wherein the polynucleotides from each of the tagged sub-samples of step (c) each comprise one of the sequence tags that identify the sub-samples and the sample identifier sequence, and wherein the sequencing reads of step (d) further comprise the sample identifier sequence.

9. The method of claim 1, wherein, in step (b) the adaptor-ligated sample is split into at least 4 sub-samples.

10. The method of claim 1, wherein the sample of step (a) comprises fragments of human genomic DNA.

11. The method of claim 1, wherein the sample of step (a) is obtained from a cancer patient.

12. The method of claim 1, further identifying a minority variant sequence in the sequence reads.

13. The method of claim 12, wherein the minority variant is a somatic mutation.

14. The method of claim 1, wherein the PCR of step (c) is composed of 4 to 20 cycles.

* * * * *